US00PP24486P2

(12) United States Plant Patent
Hurd

(10) Patent No.: US PP24,486 P2
(45) Date of Patent: May 20, 2014

(54) ***LIGULARIA* PLANT NAMED 'BOTTLE ROCKET'**

(50) Latin Name: ***Ligularia* hybrid**
Varietal Denomination: Bottle Rocket

(75) Inventor: Kevin A. Hurd, Chicago, IL (US)

(73) Assignee: Walters Garden Inc., Zeeland, MI (US)

( * ) Notice: Subject to any disclaimer, the term of this patent is extended or adjusted under 35 U.S.C. 154(b) by 183 days.

(21) Appl. No.: 13/385,115

(22) Filed: Feb. 2, 2012

(51) Int. Cl.
*A01H 5/00* (2006.01)

(52) U.S. Cl.
USPC ..... Plt./448

(58) Field of Classification Search
USPC ..... Plt./448
See application file for complete search history.

(56) References Cited

PUBLICATIONS

GTITM UPOVROM Citation for 'Bottle Rocket' as per QZ PBR 20021174; Aug. 30, 2002.*
Susan M. Martin, Walters Garden, Inc. Summer Selections 2011, May 26, 2011, p. 2, Walters Gardens, Inc., Zeeland, Michigan, USA.
Kevin A. Hurd, Plant Breeders' Rights Application, May 5, 2011, pp. 1-3, Canadian Food Inspection Agency, Canada.
Future Plants Licentie B.V., Plant Breeders' Rights Application and Grant, pp. 1-5, Community Plant Variety Office, The Netherlands, Oct. 21, 2013.

* cited by examiner

*Primary Examiner* — Kent L Bell

(57) ABSTRACT

The new and distinct cultivar of ornamental *Ligularia* plant, *Ligularia* 'Bottle Rocket' with compact habit, vertical columnar scapes producing dense clusters of golden yellow inflorescences and broad bidentate to palmatifid incised dark green leaves.

1 Drawing Sheet

Botanical classification: *Ligularia* hybrid.
Variety denomination: 'Bottle Rocket'.

BACKGROUND OF THE INVENTION

The present invention relates to the new and distinct cultivar of *Ligularia*, botanically known as *Ligularia* 'Bottle Rocket', and hereinafter referred to as the cultivar 'Bottle Rocket' or the "new plant". The new plant was discovered by Kevin A. Hurd in Zeeland, Mich., USA in the summer of 2006 as a single uninduced whole-plant mutation of *Ligularia* 'Little Rocket' U.S. Plant Pat. No. 14,621 from a group of plants growing in a trial garden environment. The plant has been asexually propagated through sterile plant tissue culture first in spring of 2007 at the same nursery in Zeeland, Mich. Subsequent asexually propagated plants have been found to be stable and identical to the original selection.

BRIEF SUMMARY OF THE PLANT

*Ligularia* 'Bottle Rocket' is unique from all other *Ligularia* known to the inventor. Other forms and cultivars have deeper reddish-brown foliage, or flowers with different scape forms or different growth habit and proportions. 'Bottle Rocket' compares most closely with its sport parent 'Little Rocket' U.S. Plant Pat. No. 14,621 but is unique in that the new plant is more compact and denser in foliage and shorter in scape height. In comparison to 'The Rocket' (not patented) the new plant is about 40% smaller in height and width at flowering. Compared to 'Little Rocket' the new plant is about 15% smaller in height and width and more compact. Leaf and scape forms are nearly identical between 'Bottle Rocket', 'Little Rocket' and 'The Rocket' with sizes of leaves increase respectively. Compared to *Ligularia*×*Hessei* 'Laternchen' U.S. Plant Pat. No. 16,026 the new plant is bidentate to palmately lobed and 'Laternchen' has smaller serrations of identical size on each leaf. The inflorescence scape is more columnar on 'Bottle Rocket' and more whorled and shorter with fewer inflorescences on 'Laternchen'. Compared to 'Britt-Marie Crawford' U.S. Plant Pat. No. 16,113 the new plant has more green foliage and more columnar scapes whereas the former has more purple foliage and corymbose inflorescence. The new plant is distinct from 'Little Rocket' and all other *Ligularia* known to the inventor through the following combined characteristics:

1. Compact foliage with dense rhizomes giving use to short foliage close together.
2. Vertical columnar scapes producing dense clusters of golden yellow flowers.
3. Bidentate to palmatifid incised leaves of primarily dark green.

BRIEF DESCRIPTION OF THE DRAWINGS

The photographs of the new plant demonstrate the unique traits and the overall appearance of *Ligularia* 'Bottle Rocket'. The colors are as accurate as reasonably possible with color reproductions. Variation in ambient light spectrum, source and direction may cause the appearance of minor variation in color. The plant used in the photographs was three-years old and was grown in a nursery trial garden in Zeeland, Mich. with 50% artificial shade and supplemental water and fertilizer when needed. No growth regulators have been used.

DETAILED BOTANICAL DESCRIPTION

Figure 1:
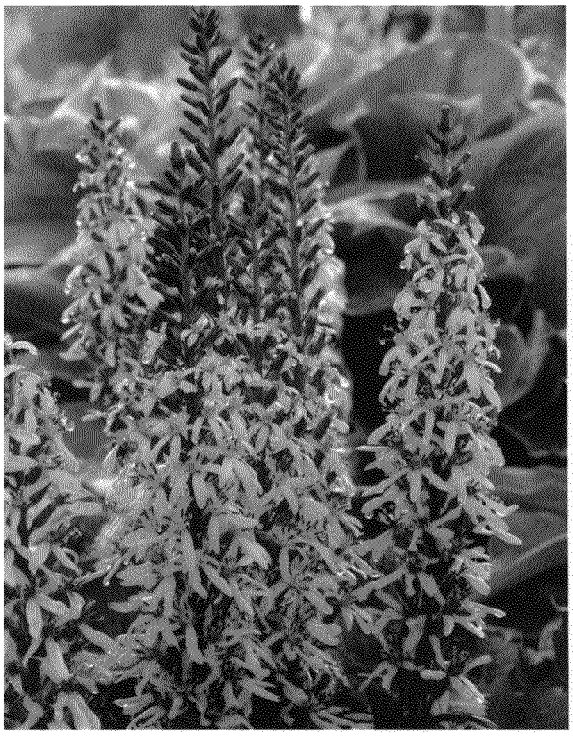
FIG. 1 shows a close-up of the flower scape.
Figure 2:
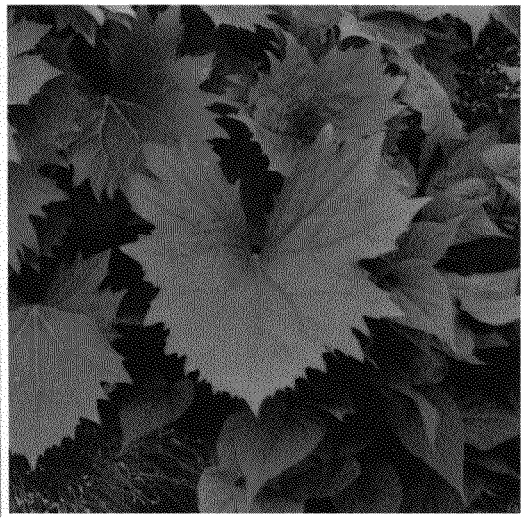
FIG. 2 shows a close-up of the leaf.
Figure 3:
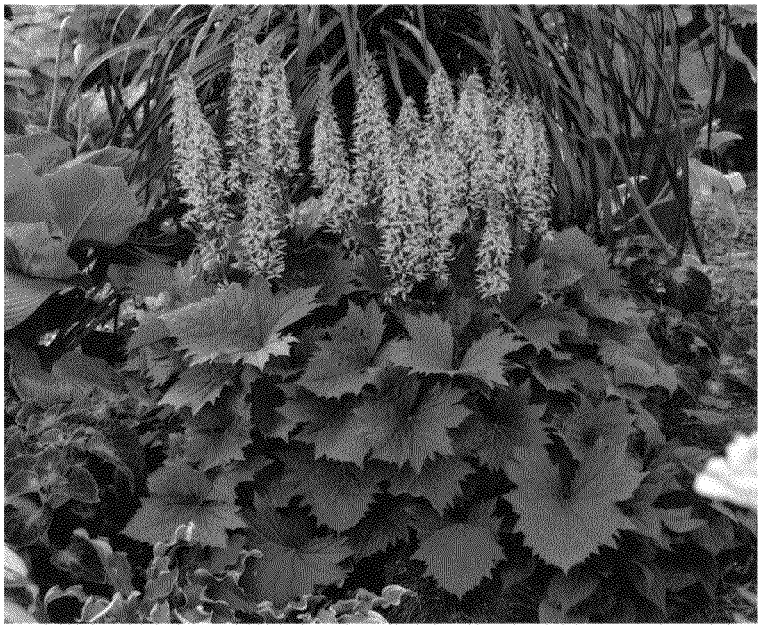
FIG. 3 shows the plant in full flower.

The following descriptions and color references except where common dictionary terms are used are based on the 2001 edition of The Royal Horticultural Society Colour Chart. *Ligularia* 'Bottle Rocket' has not been observed under all possible environments. The phenotype may vary slightly with different growing environments such as temperature, light, fertility, soil pH, moisture and plant maturity levels, but without any change in the genotype. The following observations and size descriptions are based on three-year old plants growing in a 50% shaded trial garden in Zeeland, Mich. Plants were given supplemental water and fertilizer but no plant growth regulators were used.

Botanical classification: *Ligularia* hybrid.

Parentage: *Ligularia* 'Little Rocket'.

Plant habit: Hardy herbaceous perennial; rhizomatous, mounded foliage with flowers spirally arranged on dense raceme above foliage; plant height about 100 cm tall in flower; plant width about 90 cm at widest point at initial flower level.

Growth rate: Moderately vigorous finishing in a 3.8 liter container from a 65 mm plug in about 7 weeks and finishing in a 65 mm plug from a rooted Stage 3 tissue culture explants in about 10 weeks.

Root: Fine, less than 0.5 mm diameter, heavily branched; color dependant on soil type, usually white to light cream with a tint of nearest RHS N186C.

Stem: About 20 per plant; vertical; about 100 cm long and 8 mm diameter at base; secondary branches to about 11 cm long and 2 mm diameter; angle of secondary branches tight against main peduncle, vertical; color mix of nearest RHS N144C and RHS N187A; with short white pubescence nearest RHS155C about 0.5 mm long.

Internode: Average about 12 cm.

Foliage: Glabrous, acaulescent or nearly so with cauline leaves on raceme.

Leaf blade: Bidentate to palmatifid; irregularly coarsely dentate margin; acute apex; hastate to sagittate base; average 17 lobes per leaf; average axillary lobe 5.4 cm long and 3.4 cm wide; average terminal lobe 6.7 cm long and 6.4 cm wide; total leaf blade about 16 cm long and 18 cm wide.

Leaf blade color: Adaxial side nearest RHS 137A; abaxial surface between RHS 138B and RHS 138C but closer to RHS 138B.

Veins: Palmate, impressed on adaxial surface and ridged on abaxial surface.

Vein color: Adaxial main vein between RHS N186C and RHS 187A, with secondary veins 186A and 203B; abaxial veins nearest RHS 148C with slight tinting of RHS N186C toward petiole.

Petiole: Cylindrical, pubescent, glaucous; about 40.0 cm long and 6.0 mm diameter; petioles on cauline leaves shorter to about 23 cm and about 4 mm in diameter, diminishing in length distally.

Petiole color: Nearest RHS 148B with tinting of nearest N187A intensifying in the distal 4.0 to 5.0 cm near leaf blade.

Flower description:

Inflorescence: Composite head of ray and disc florets; average size flowering portion of spike 40.0 cm long and 5.0 cm across; about 95 inflorescences per raceme; with additional occasional branching in the lower few nodes of about 3 to 7 inflorescences per branch; flower timing in Michigan begins late June and continues for about four weeks on the plant.

Buds about two days prior to dehiscence and while showing ray floret color: Narrowly oblong; about 12 mm long and 4 mm diameter, narrowly oblong, obtuse apex, obtuse base.

Bud color: Nearest RHS 138A with heavy tinting of RHS N187A.

Flower: Projected upwardly and outwardly; zygomorphic; average size 4.0 cm across and 3.0 cm deep; average longevity on the plant, one week; self-cleaning; consisting of usually four ray florets and approximately 15 disc inflorescences; receptacle size about 5.0 mm diameter and 8 mm deep; fragrance has not been noted.

Ray floret: Usually four per composite head; imperfect, pistillate.

*Ligule*.—One per inflorescence, oblanceolate, entire, apex emarginate usually producing three lobes of unequal sizes from indentations about 2.0 mm and 1.0 mm deep; base attenuate; glaucous and glabrous both surfaces; curved slightly toward base; about 2.5 cm long and 4.0 mm wide at middle, tapering to less than 1.0 mm at base.

*Ligule color*.—Nearest RHS 14B on adaxial and RHS 12D on abaxial side.

*Pistil*.—Single, stigma split in two in distal 1.5 mm and curling around nearly 360 degrees; style about 8.0 mm long and less than 0.5 mm diameter; style and stigma color beginning nearest RHS 14C and maturing to nearest RHS 187A.

*Ovary color*.—Nearest RHS N144A.

Disc floret: About 15 per head arranged in center of receptacle; perfect; tubular.

*Corolla*.—Usually five, about 8.0 mm long and 1.0 mm diameter; fused into tube except distal 0.5 mm; acute apex; nearest RHS 23B both surfaces.

*Androecium*.—Usually five linear anthers about 3.0 mm long and fused into tube around style; nearest RHS N186C; filament: five, thin, about 3.0 mm long and less than 0.5 mm diameter; pollen has not been observed.

*Pistil*.—Single, stigma split in two in distal 1.5 mm and curling around nearly 360 degrees in maturity; style about 7.0 mm long and less than 0.5 mm diameter; style and stigma color beginning nearest RHS 14C and maturing to nearest RHS 187A.

*Ovary color*.—Nearest RHS N144A.

Pappus: Hair-like, fine, numerous about 60 to 80 per inflorescence; about 6.0 mm long and less than 0.1 mm diameter, nearest RHS 161B.

Involucral bracts: Usually eight in single whorl; about 8.0 mm long and 2.0 mm wide; linear; acute apex and base fused; margin entire; glabrous; color nearest RHS 137A with tinting of RHS 200B on adaxial and abaxial surfaces.

Peduncle: About 20 per plant; vertical; about 100 cm long and 8 mm diameter at base; secondary branches to about 11 cm long and 2 mm diameter; angle of secondary branches tight against main peduncle, vertical; color mix of nearest RHS N144C and RHS N187A; with short white pubescence nearest RHS155C about 0.5 mm long.

Pedicel: Average 5 mm long and 1 mm diameter; angle 85° from vertical, strong, greyed-purple RHS 187B to RHS 187C; with minute pubescence of about 0.1 mm and RHS 155C.

Fruit: No fruit or seed have yet been observed.

Hardiness, pest and disease resistance: The new plant grows best with ample moisture, adequate drainage and shade from hot sun. Hardiness at least from USDA zone 4 through high temperatures of 36° C. Disease and pest resistance beyond what is typical of that of other *Ligularia* has not been observed.

I claim:

1. A new and distinct cultivar of ornamental *Ligularia* plant, *Ligularia* 'Bottle Rocket', as herein described and illustrated, suitable as a potted plant, cut flower, for the garden as an accent or en masse.

* * * * *